United States Patent
Teissonniere et al.

(10) Patent No.: US 11,842,818 B2
(45) Date of Patent: Dec. 12, 2023

(54) CONTACT TRACING AMONG WORKERS AND EMPLOYEES

(71) Applicant: Noodle Technology Inc., San Francisco, CA (US)

(72) Inventors: Eliott Quentin Eric Teissonniere, San Francisco, CA (US); Lucien Jean Baptiste Loiseau, San Francisco, CA (US); Garrett Edward Kinsman, San Francisco, CA (US); Micha Anthenor Benoliel, San Francisco, CA (US)

(73) Assignee: Noodle Technology Inc., San Francisco, CA (US)

(*) Notice: Subject to any disclaimer, the term of this patent is extended or adjusted under 35 U.S.C. 154(b) by 274 days.

(21) Appl. No.: 17/244,749

(22) Filed: Apr. 29, 2021

(65) Prior Publication Data
US 2021/0350938 A1    Nov. 11, 2021

Related U.S. Application Data

(60) Provisional application No. 63/021,040, filed on May 6, 2020.

(51) Int. Cl.
*G16H 50/80* (2018.01)
*G06F 21/62* (2013.01)
(Continued)

(52) U.S. Cl.
CPC ......... *G16H 50/80* (2018.01); *G06F 21/6254* (2013.01); *H04L 9/085* (2013.01); *H04L 9/3006* (2013.01)

(58) Field of Classification Search
CPC ..... G16H 50/80; G06F 21/6254; H04L 9/085; H04L 9/3006
See application file for complete search history.

(56) References Cited

U.S. PATENT DOCUMENTS

| 10,448,238 B2 | 10/2019 | Benoliel et al. |
| 2012/0260324 A1* | 10/2012 | Lenon .................. G06Q 20/385 726/6 |

(Continued)

FOREIGN PATENT DOCUMENTS

| CN | 111446006 A * | 4/2020 | ............... H04L 9/08 |
| EP | 3907928 A1 * | 11/2021 | ........... H04L 9/0841 |

(Continued)

OTHER PUBLICATIONS

Ollikaine, Ville, Halunen, Kimmo, Rendezvous based pandemic tracing by sharing Diffie-Hellman generated common secrets, VTT technical Research Center of Finland, Apr. 9, 2020 (Year: 2020).*

(Continued)

*Primary Examiner* — Darshan I Dhruv (74) *Attorney, Agent, or Firm* — Buchalter; Jason W. Croft (57) ABSTRACT

A method may include collecting from each of multiple endpoint devices a set of anonymized interactions of the corresponding endpoint device with other endpoint devices. Each anonymized interaction in the set of anonymized interactions may be based on an ephemeral unique identifier of another endpoint device involved in a corresponding anonymized interaction with the corresponding endpoint device. The method may include, for each endpoint device, resolving identities of the other endpoint devices with which the corresponding endpoint device has interacted from the corresponding set of anonymized interactions.

18 Claims, 5 Drawing Sheets

(51) Int. Cl.
  *H04L 9/08* (2006.01)
  *H04L 9/30* (2006.01)

(56) References Cited

U.S. PATENT DOCUMENTS

| | | | |
|---|---|---|---|
| 2014/0162601 A1* | 6/2014 | Kim | H04W 8/005 |
| | | | 455/411 |
| 2017/0209102 A1* | 7/2017 | Parthasarathy | A61B 5/0059 |
| 2018/0052970 A1* | 2/2018 | Boss | G06F 21/35 |
| 2019/0357040 A1 | 11/2019 | Benoliel et al. | |
| 2020/0077246 A1* | 3/2020 | Mars | G06Q 40/02 |
| 2021/0058376 A1 | 2/2021 | Teissonniere et al. | |

FOREIGN PATENT DOCUMENTS

| | | | |
|---|---|---|---|
| WO | WO-2019246206 A1 * | 12/2019 | H04L 9/006 |
| WO | WO-2021041279 A1 * | 3/2021 | H04L 63/0421 |
| WO | WO-2021225497 A1 * | 11/2021 | |

OTHER PUBLICATIONS

Ville et al. Rendezvous based pandemic tracing by sharing Diffie-Hellman generated common secrets (Year: 2020).*
International Search Report and Written Opinion in PCT/US2021/029991 dated Aug. 4, 2021.
Loiseau, et al. "Whisper Tracing Version 3—an open and privacy first protocol for contact tracing" Whitepaper, Nodle, Mar. 31, 2020.
Markku-Juhani O. Saarinen and Jean-Philippe Aumasson, The BLAKE2 Cryptographic Hash and Message Authentication Code (MAC), RFC 7693, Nov. 2015, DOI: 10.17487/RFC7693.
P. Levis et al., The Trickle Algorithm, RFC 6206, Mar. 2011, DOI: 10.17487/RFC6206.

* cited by examiner

CONTACT TRACING AMONG WORKERS AND EMPLOYEES

CROSS-REFERENCE TO RELATED APPLICATION

This application claims the benefit of and priority to U.S. Provisional App. No. 63/021,040 filed May 6, 2020, which is incorporated herein by reference in its entirety.

FIELD

The embodiments discussed herein are related to contact tracing among workers and employees.

BACKGROUND

The world is currently in the midst of the covid-19 global pandemic. Across the globe, efforts are being made to stop the spread of the covid-19 virus by flattening the curve through social distancing measures and mask wearing. In many cases, efforts to deploy these distancing methods have led national governments to conclude that halting the spread requires a full lockdown of the local population, and acceptance of the devastating effects this will have on both the local population and the economy.

Another method known as contact tracing aims at enforcing targeted home quarantine. However, this first requires the ability to identify infection clusters as well as people who have been exposed to infected individuals. The challenge with this approach is that someone infected by the virus can go unnoticed for up to 20 days before showing symptoms or testing positive. During this time, that person may have interacted with many other individuals and passed the disease on to them.

The claimed subject matter is not limited to embodiments that solve any disadvantages or that operate only in environments such as those described above. This background is only provided to illustrate examples of where the present disclosure may be utilized.

SUMMARY

The present disclosure generally relates to contact tracing among workers and employees.

In one aspect of the disclosure, a method includes collecting from each of multiple endpoint devices a set of anonymized interactions of the corresponding endpoint device with other endpoint devices. Each anonymized interaction in the set of anonymized interactions is based on an ephemeral unique identifier of another endpoint device involved in a corresponding anonymized interaction with the corresponding endpoint device. The method includes, for each endpoint device, resolving identities of the other endpoint devices with which the corresponding endpoint device has interacted from the corresponding set of anonymized interactions.

Another aspect of the disclosure may include any combination of the above-mentioned features and may further include precomputing ephemeral unique identifiers for each endpoint device and storing the precomputed ephemeral unique identifiers for each endpoint device. Each anonymized interaction may include an ephemeral unique identifier of a corresponding one of the other endpoint devices with which the corresponding device has interacted. Resolving identities of the other endpoint devices with which the corresponding device has interacted may include searching for ephemeral unique identifiers from the anonymized interactions in the stored precomputed ephemeral unique identifiers.

Another aspect of the disclosure may include any combination of the above-mentioned features and may further include the resolving identities of the other endpoint devices with which the corresponding device has interacted further including, in response to a given anonymized interaction matching a given stored precomputed ephemeral unique identifier that is associated with a given endpoint device, determining that the corresponding endpoint device interacted with the given endpoint device.

Another aspect of the disclosure may include any combination of the above-mentioned features and may further include each endpoint device has a corresponding secret key known to a network operator and each ephemeral unique identifier is precomputed based at least in part on a corresponding secret key and a counter.

Another aspect of the disclosure may include any combination of the above-mentioned features and may further include the precomputing ephemeral unique identifiers including, for each endpoint device: generating multiple deterministic seeds from the corresponding secret key and multiple counter values and generating multiple ephemeral public key pairs from the deterministic seeds. Each precomputed ephemeral unique identifier may include a different one of the ephemeral public key pairs.

Another aspect of the disclosure may include any combination of the above-mentioned features and may further include the generating the deterministic seeds including generating multiple hash values. Each hash value may be a hash of the corresponding secret key and a different counter value.

Another aspect of the disclosure may include any combination of the above-mentioned features and may further include the generating the ephemeral public key pairs including generating multiple Curve25519 public keys, each Curve25519 public key generated using a different deterministic seed as input.

Another aspect of the disclosure may include any combination of the above-mentioned features and may further include determining whether a first user of the corresponding endpoint device was exposed to a second user of another endpoint device based on whether an identity of the other endpoint device is among the resolved identities of the other endpoint devices with which the corresponding endpoint device has interacted.

Another aspect of the disclosure may include any combination of the above-mentioned features and may further include the endpoint devices being borne by users at a job site, the method further including determining, based on interactions with endpoint devices having known locations within the job site, at least one of: one or more patterns of movement of the users at the job site, analytics regarding frequency of visits by users to each of one or more locations within the job site, or analytics regarding number of interactions between the users at each of one or more locations within the job site.

Another aspect of the disclosure may include any combination of the above-mentioned features and may further include a non-transitory computer-readable storage medium having computer-readable instructions stored thereon that are executable by a processor to perform or control performance of the method.

Another aspect of the disclosure may include any combination of the above-mentioned features and may further include, or may stand alone by including, generating, over time, multiple ephemeral unique identifiers for a first endpoint device, each of the ephemeral unique identifiers being specific to the first endpoint device and configured to identify the first endpoint device; scanning for other endpoint devices; and in response to detecting a second endpoint device while scanning: providing a current ephemeral unique identifier of the first endpoint device to the second endpoint device; and receiving a current ephemeral unique identifier of the second endpoint device at the first endpoint device.

Another aspect of the disclosure may include any combination of the above-mentioned features and may further include adding an anonymized interaction with the second endpoint device to a set of anonymized interactions of the first endpoint device with other endpoint devices. Each anonymized interaction in the set of anonymized interactions may be based on a corresponding ephemeral unique identifier of the corresponding endpoint device received during a corresponding interaction between the first endpoint device and the corresponding endpoint device.

Another aspect of the disclosure may include any combination of the above-mentioned features and may further include sharing the set of anonymized interactions of the first endpoint device with a backend server to resolve identities of the other endpoint devices with which the first endpoint device has interacted.

Another aspect of the disclosure may include any combination of the above-mentioned features and may further include the first endpoint device having a secret key known to a network operator and each of the ephemeral unique identifiers for the first endpoint device being based on the secret key and a counter.

Another aspect of the disclosure may include any combination of the above-mentioned features and may further include the generating, over time, the ephemeral unique identifiers including, for each of the ephemeral unique identifiers: generating a deterministic seed from the secret key and a counter value that depends on a time at which the deterministic seed is generated and generating an ephemeral public key pair from the deterministic seed to use as a corresponding one of the ephemeral unique identifiers.

Another aspect of the disclosure may include any combination of the above-mentioned features and may further include the generating the deterministic seed including generating a hash value as a hash of the secret key and the counter value.

Another aspect of the disclosure may include any combination of the above-mentioned features and may further include the counter value including a value of a difference between a current time and a reference time divided by a time step.

Another aspect of the disclosure may include any combination of the above-mentioned features and may further include the generating the ephemeral public key pair including generating a Curve25519 public key using the deterministic seed as input.

Another aspect of the disclosure may include any combination of the above-mentioned features and may further include determining a distance between the first endpoint device and the second endpoint device and in response to the distance being less than a threshold, outputting an alert to a user of the first endpoint device.

Another aspect of the disclosure may include any combination of the above-mentioned features and may further include a non-transitory computer-readable storage medium having computer-readable instructions stored thereon that are executable by a processor to perform or control performance of the method.

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

DETAILED DESCRIPTION

Reference will be made to the drawings and specific language will be used to describe various aspects of the disclosure. Using the drawings and description in this manner should not be construed as limiting its scope. Additional aspects may be apparent in light of the disclosure, including the claims, or may be learned by practice.

Some embodiments herein relate to contact tracing among workers and employees. Embodiments may provide a relatively small electronic device to employees, workers, inhabitants, visitors, or the like at a given worksite, job site, location, or the like. These small electronic devices may be referred to hereinafter as endpoint devices. When individuals bearing such endpoint devices are in proximity to each other, they may exchange information that can later be used to identify contacts, or interactions, each electronic device (and thus each user) has had with other electronic devices (and thus other users). The endpoint devices may upload their data to a backend server to resolve identities of other endpoint devices involved in interactions with each endpoint device. The data may be uploaded using a delay tolerant networking approach, such as described in U.S. Pat. No. 10,448,238 for DELAY TOLERANT DECENTRALIZED NETWORK, which is incorporated herein by reference in its entirety. Alternatively, the data may be uploaded at other times and/or in association with one or more events, such as when the endpoint device is plugged into an adapter or dock for recharging purposes, when the endpoint device is left at one or more predetermined locations, when the endpoint device passes through or by one or more predetermined locations (e.g., a door, a locker room, or the like).

The endpoint device may periodically send or upload this data to another device, such as to a smartphone, router, computer, server, cellular tower, or the like. The endpoint device may structure or encode the data in a manner such that the data is small and uses a relatively small amount of battery life for data storage and data transmission. The endpoint device may also generally function in a low-power state. For example, the endpoint device may not collect data while at rest. The endpoint device may include a trigger, such as an accelerometer, to detect motion. The detected motion may trigger a data collection and/or data transmission mode, after which the endpoint device may reenter the low power state.

The endpoint device may be employed with or paired to a smartphone app or may be implemented in a standalone arrangement to enhance the efficiency of such a solution. The endpoint device may be clipped to a user's belt, worn around the neck, wrist, or on a backpack, or the like.

The endpoint device may broadcast an encrypted and/or anonymous and/or random identifier (ID), scan for other nearby IDs (e.g., other endpoint devices), and offload data to the cloud and/or the backend server via a network. The endpoint device may share further encrypted peer to peer data beyond IDs, such as sensor data (e.g., temp, light, humidity, pressure, radiation, $O_2$, $CO_2$, CO, $CH_4$, acceleration, heart rate, neuron activity), positional or location information, maps, messages, status, or the like.

One or more nearby intermediate devices (e.g., smartphones, routers) may be used together as a system to form a peer to peer mesh network, with an optional external omnidirectional or directional antenna using wireless protocols beyond bluetooth (such as Wi-fi, LTE, or collaborative radio) to build wireless IP backhauls. The intermediate device(s) may become an offline node in the network and receive cryptocurrency rewards for its participation.

The endpoint device may be powered by a battery and/or may be rechargeable through a charge port or data (e.g., USB-C). Alternatively or additionally, the endpoint device may include energy harvesting components and/or capabilities, some examples of which are described elsewhere herein.

The endpoint device may interact through an application programming interface (API) to the cloud and/or the backend server, but may support interaction with a smartphone or other device directly. User input and/or output with the endpoint device may be made through LEDs on the endpoint device, device vibrations (e.g., via a haptic device), tapping the endpoint device, or the like.

The endpoint device may include firmware that collects nearby radio signals (e.g., Bluetooth® low energy (BLE) beacons) and saves them locally in the event they can't be shared right away. For example, they may be saved on a flash memory. Alternatively or additionally, the firmware may include or implement any storage algorithm that would fit, such as but not limited to a native writing of the data or a Time Aware Least Recent Used (TLRU) Cache.

The endpoint device may broadcast its own ID that may rotate based on a given algorithm over time to protect privacy of the user.

At some point in time the collected identifiers at each endpoint device are uploaded to the backend server, which may be running on a third party cloud or on server of an organization deploying the contact tracing solution.

In some embodiments, the endpoint device may monitor the distance between it and other endpoint devices. For example, the distance may be monitored through a time of flight based protocol. The endpoint device may provide an alert feedback to the user through a visual indicator (e.g., flashing LEDs), haptic feedback (e.g., vibration), or other output.

The data collected by each endpoint device may be uploaded to the backend server through one or more intermediate devices, such as BLE routers that may be deployed at one or more locations within a worksite (or jobsite, or the like), or smartphones of the workers (or employees, etc.).

The backend server may aggregate IDs and their interactions with other IDs or any other data shared by the endpoint devices. The backend server may aggregate them under the identity of the corresponding users or not. The backend server may then expose them over an API, push them through a webhook, or show them on a graphical interface to any administrators. It can be used to analyze how people behave in the workplace, to send alerts, to understand how employees or other individuals move on a job site, to provide analytics on the most frequented places or where the most contacts occur, the like.

Figure 1:
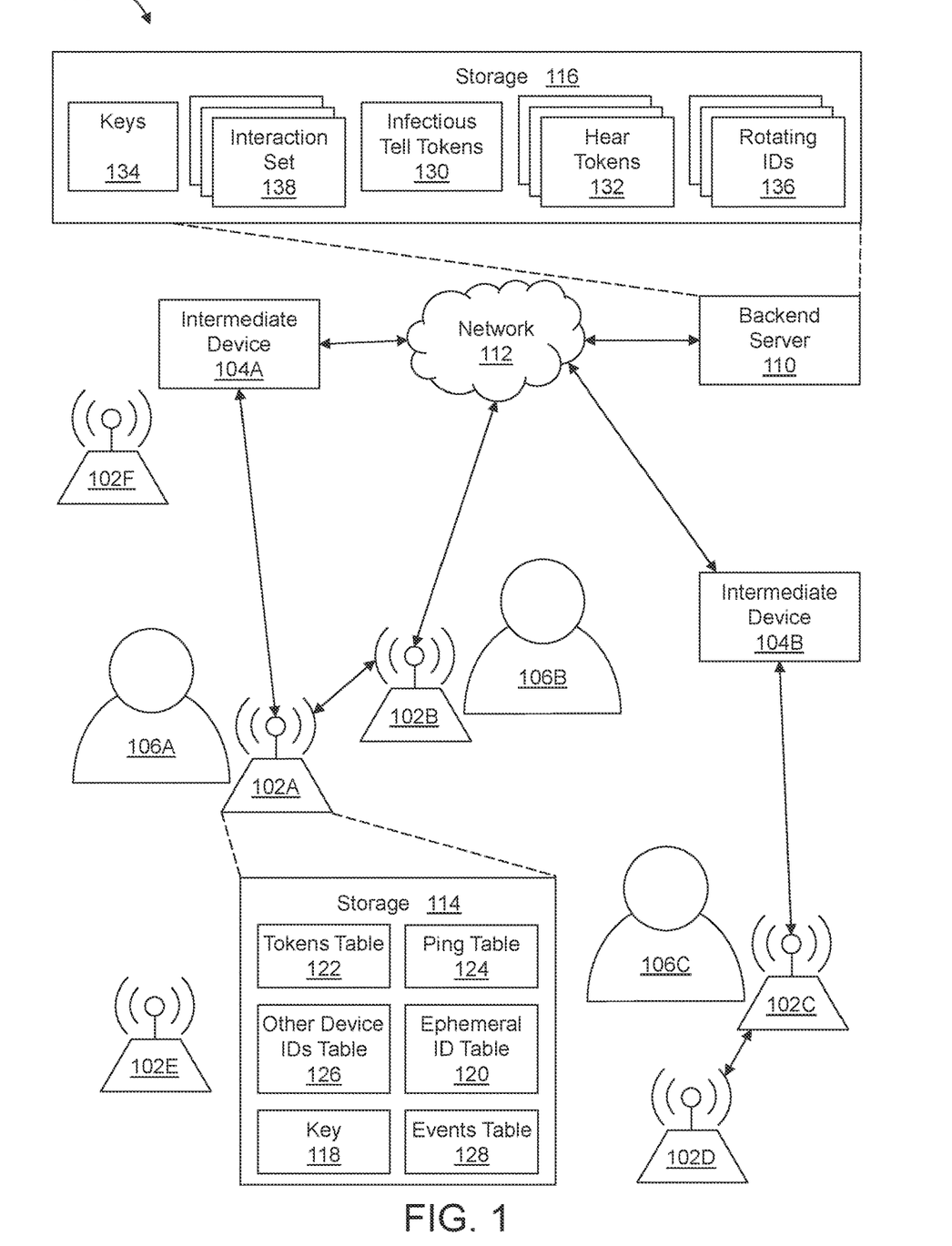
FIG. 1 illustrates an example operating environment 100 in which embodiments of the present disclosure may be implemented.

FIG. 1 illustrates an example operating environment 100 in which embodiments of the present disclosure may be implemented. The operating environment 100 may include one or more endpoint devices 102A-102F (collectively "endpoint devices 102" or generically "endpoint device 102"), one or more intermediate devices 104A-104B (collectively "intermediate devices 104" or generically "intermediate device 104"), one or more users 106A-106C (collectively "users 106" or generically "user 106"), a backend server 110, and a network 112. In some embodiments, contact tracing between users 106 may be enabled within the operating environment 100.

In general, the network 112 may include one or more wide area networks (WANs) and/or local area networks (LANs) that enable the endpoint devices 102, the intermediate devices 104, and/or the backend server 110 to communicate with each other. In some embodiments, the network 112 may include the Internet, including a global internetwork formed by logical and physical connections between multiple WANs and/or LANs. Alternately or additionally, the network 112 may include one or more cellular radio frequency (RF) networks and/or one or more wired and/or wireless networks such as 802.xx networks, Bluetooth® access points, wireless access points, Internet Protocol (IP)-based networks, or other wired and/or wireless networks. The network 112 may also include servers that enable one type of network to interface with another type of network.

Each endpoint device 102 may include one or more Internet of Things (IoT) devices. Each endpoint device 102 may include a power supply, a network device, and optionally a data collection device (e.g., a sensor). The power supply may include a battery or a connection to a power grid. Additionally or alternatively, the power supply may include an energy harvesting apparatus, such as a solar panel, solar cell, solar photovoltaic, electromagnetic, inductive charger, charging port, betavoltaic device, thermoelectric generator, nanogenerator, or the like. In at least some embodiments, the endpoint device 102 may not include a power supply and may instead use ambient backscatter techniques. One or more of the endpoint devices 102 may also include one or more sensors. The one or more sensors may be configured to detect any type of condition, and generate electronic data based on a detected condition. For example, one or more of the endpoint devices 102 may include a smart watch with a heart rate monitor that is configured to generate heart rate data using heart rate conditions collected by the heart rate monitor. In some embodiments, one or more of the endpoint devices 102 does not have capability to communicate over the Internet and only includes hardware and/or software capable of communicating with nearby devices, such as a nearby intermediate device 104. In other embodiments, the endpoint device 102 may include hardware and/or software to communicate over the Internet.

The network device of the endpoint device 102 may include any hardware, software, or combination thereof that is capable to communicate with another device via a network. In at least one embodiment, the network device may include any network controller configured to communicate via a short-range network, such as Bluetooth® or any other short-range network. In at least one embodiment, the network device may include any network controller configured to communicate via a low-power network. Example endpoint devices 102 include, industrial devices, residential appliances, commercial equipment, inventory trackers, smart watches, wearables, heart rate monitors, logistics trackers, environmental sensors, cash registers, credit card readers, point-of-sale (POS) terminals, bikes, electric scooters, electric skate boards, cars, electric cars, satellites, or any device (mobile or not mobile) that includes a wireless radio interface. The operating environment 100 may include any number of endpoint devices 102 and the endpoint devices 102 in the operating environment 100 may be any type of endpoint device 102, including any type of network-capable device. The endpoint devices 102 may be fixed or relatively stationary in the operating environment 100, such as a POS terminal or a pollution sensor. Additionally or alternatively, the endpoint devices 102 may be mobile, such as a smart watch, or any car or vehicle.

In at least one embodiment, each of the endpoint devices 102A-102C is mobile and is configured to be borne (e.g., worn, carried) by a user, such as the users 106A-106C, while each of the endpoint devices 102D-102F is fixed. Any of the endpoint devices 102A-102C may be clipped to a belt of the user 106, worn as a pendant (e.g., attached to lanyard worn around a neck of the user 106), worn on a wrist of the user 106, carried in a pocket of the user 106, attached to a backpack of the user 106, or may otherwise be borne by the user 106. The endpoint devices 102D-102F may be attached to stationary objects or structures (e.g., a wall) and/or may be at locations known to a network operator that operates a network of endpoint devices to which the endpoint devices 102 belong. The endpoint devices 102 may be owned by, leased by, or otherwise associated with a particular business, corporation, or other entity. The endpoint devices 102A-102C may be provided to employees or other individuals (e.g., the users 106) at a job site and their interactions with each other and/or with the endpoint devices 102D-102F may be tracked for contact tracing or other purpose(s).

The one or more endpoint devices 102 may be configured to communicate with other devices according to any suitable wireless communication standard or technology, such as Bluetooth®, Bluetooth® Low Energy (BLE), any of the 802.11 protocols (commonly referred to as Wi-Fi®), or the like or any combination thereof. In some embodiments, one or more of the endpoint devices 102 may broadcast a beacon, scan for beacons, connect with other devices, exchange ephemeral unique identifiers, and/or otherwise communicate with other devices. For example, when the users 106A, 106B are bearing the endpoint devices 102A, 102B and come within proximity of each other (e.g., close enough for endpoint devices 102A, 102B to communicate), the endpoint devices 102A, 102B may wirelessly connect and exchange ephemeral unique identifiers. Each of the endpoint devices 102A-102F may operate in a similar manner when in proximity to another endpoint device 102 or potentially other devices. When ephemeral unique identifiers are exchanged, each endpoint device 102 may store the ephemeral unique identifiers it receives and/or may generate one or more interaction tokens from the ephemeral unique identifiers. The ephemeral unique identifiers and/or the interaction tokens may be used at the corresponding endpoint device 102 and/or the backend server 110 to contact trace among users 106, track movement patterns of users 106, and/or for other purposes.

The one or more intermediate devices 104 may include any type of device capable of communicating with the endpoint device 102 and the backend server 110. In at least one embodiment, the intermediate device 104 may include two network controllers, including a first network controller to communicate via a first wireless technology (e.g., BLE) with the endpoint devices 102 and a second network controller to communicate via a second wireless technology (e.g., Wi-Fi®) with the backend server 110. Example intermediate devices 104 include mobile devices, personal computers (PC), laptops, smart phones, netbooks, e-readers, personal digital assistants (PDA), cellular phones, mobile phones, tablets, vehicles, drones, cars, trucks, wearable devices, routers, televisions, set top boxes, or the like.

In some embodiments, one or more of the endpoint devices 102 may communicate with the backend server 110 through the network 112. For example, the bidirectional arrows in FIG. 1 between the endpoint device 102B and the network 112 and between the network 112 and the backend server 110 indicates that the endpoint device 102B can communicate with the backend server 110 through the network 112. In some embodiments, one or more of the endpoint devices 102 may be a relatively small device and/or with limited processing and/or networking capabilities. For example, the endpoint devices 102A, 102C may have a single network controller, e.g., a BLE network controller, for relatively short-range communication and may communicate with the backend server 110 through the intermediate device 104. More generally, any of the endpoint devices 102A-102F may communicate with the backend server 110 directly through the network 112 or less directly through the intermediate device 104A and the network 112, depending on the networking capabilities of the endpoint device 102.

One or more of the endpoint devices 102 and the backend server 110 may include or be coupled to one or more computer-readable storage media (hereinafter "storage"), such as flash memory devices (e.g., solid state memory devices), Random Access Memory (RAM), Read-Only Memory (ROM), Electrically Erasable Programmable Read-Only Memory (EEPROM), or any other storage medium which may be used to carry or store desired program code in the form of computer-executable instructions or data structures. Combinations of the above may also be included within the scope of storage. FIG. 1 illustrates an example storage 114 included in or coupled to the endpoint device 102A. The other endpoint devices 102 may similarly include or be coupled to storage. FIG. 1 additionally illustrates an example storage 116 included in or coupled to the backend server 110. Data stored in the storage 114, 116 may be used for or in connection with a contact tracing algorithm. An example contact tracing algorithm that may be implemented in the operating environment 100 will now be described.

Some embodiments of the contact tracing algorithm may alert individuals about their exposure to a biological threat (e.g., covid-19) while protecting the user's privacy and associated data. Users 106 may opt-in to an associated contact tracing service. Interactions with peers may be recorded privately and locally (e.g., on endpoint devices 102A-102C) and interactions with back-end services (e.g., the backend server 110) may be voluntary. Some embodiments may operate without linking data to any privately identifiable information and may be resilient against compromise or leakage. For example, the endpoint devices 102 may share anonymous and unlinkable identities with each other and with the backend server 110 to reduce or eliminate the likelihood that, even in the event of a data leak, meaningful information may be extracted from the data leak. Alternatively or additionally, information shared among the endpoint devices 102 and/or the backend server 110 may be timestamped so that older data, e.g., data outside a given window of relevance, may be deleted to reduce storage overhead.

To detect contacts, or interactions, the endpoint devices 102 may exchange unique identifiers (IDs) with each other. The unique IDs may include public keys or other suitable unique IDs. The exchange may occur over a BLE connection or other suitable wireless connection. In some embodiments, the endpoint devices 102 may advertise or broadcast their unique IDs to any other endpoint devices 102 in close proximity. For BLE, "close proximity" may be within 20 meters of each other, within 10 meters of each other, or within some other relatively short distance of each other. In FIG. 1, the endpoint devices 102A, 102B are depicted in close proximity and exchanging unique IDs with each other. Similarly, the endpoint devices 102C, 102D are depicted in close proximity and exchanging unique IDs with each other.

To protect the users 106 from inadvertently leaving a trail, the endpoint devices 102 may periodically, randomly, pseudo-randomly, according to a schedule, or in some other manner re-generate their unique IDs. This may also be described as rotating their IDs. The unique IDs used by a given endpoint device 102 may be referred to as ephemeral unique IDs or rotating IDs since they are not fixed or permanent in time.

An example will now be discussed in which the ephemeral unique IDs are ephemeral public keys (e.g., of corresponding ephemeral private public keypairs). The ephemeral unique IDs may be generated in some other manner in other embodiments. In some embodiments, ephemeral private public keypairs may be generated randomly or as the output of a Key Derivation Function, as described below.

Some embodiments may generate a deterministic seed I as a hash H based on one or more deterministic parameters. The hash may then later be used as a seed for a keypair generation function. In an example, the deterministic seed $I_C$ is generated according to equation 1:

$$I_C = H_{blake2b\text{-}160}(S, C) \qquad \text{Equation 1}$$

In equation 1, C is a counter, S is a secret key known to a corresponding endpoint device 102 and the backend server 110 (or more generally a network operator), and $H_{blake2b\text{-}160}$ is a cryptographic hash as disclosed in Markku-Juhani O. Saarinen and Jean-Philippe Aumasson, *The BLAKE2 Cryptographic Hash and Message Authentication Code (MAC)*, RFC 7693, November 2015, DOI: 10.17487/RFC7693, which is incorporated herein by reference in its entirety. Other hash functions and/or parameters may be used. Some embodiments use time as a parameter and calculate C at any given time now (hereinafter $C_{now}$) from three time-related parameters—a time reference $T_{Reference}$, a time step $T_{step}$, and any given time now—according to equation 2:

$$C_{now} = \text{floor}[(\text{now} - T_{Reference})/\text{Step}] \qquad \text{Equation 2}$$

In equation 2, floor[ ] is the floor function.

Substituting equation 2, e.g., $C_{now}$, in place of C in equation 1 yields equation 3:

$$I_{now} = H_{blake2b\text{-}160}(S, \text{floor}[(\text{now} - T_{Reference})/T_{Step}]) \qquad \text{Equation 3}$$

Equation 3 generates the deterministic seed at any given time, $I_{now}$, as a blake2b digest of the secret key S and $C_{now}$.

Parameters of the $H_{blake2b\text{-}160}$ cryptographic hash according to an example embodiment herein are provided in Table 1:

TABLE 1

| Secure ID blake2b Parameters | |
| --- | --- |
| Key | 256-bits random |
| Salt | C as 128-bits |
| Parameters | ~WhisperSecureId |

In some embodiments, the deterministic seed $I_{now}$ may be used in a keypair generation function to generate an ephemeral public key pair $PK_i$ according to equation 4:

$$K_i = \text{Curve25519}(I_{now}) \qquad \text{Equation 4}$$

The endpoint devices 102 may use a common basepoint 9 in the generation of ephemeral public key pairs $PK_i$. Each of the endpoint devices 102 may generate ephemeral public keys as described herein or other ephemeral unique IDs and may exchange them with each other for contact tracing.

To discover new peers, each endpoint device 102 may both advertise its presence by periodically broadcasting a beacon and perform periodic scans of its neighborhood to detect beacons of other peers (e.g., other endpoint devices 102). The endpoint devices 102 may advertise themselves using BLE advertising data or other suitable data. Each endpoint devices 102 may include a contact tracing service UUID in its beacon to advertise its support for the contact tracing algorithm. The process of initiating a connection between two co-located endpoint devices 102 may be optimized so that only one of them elects to initiate the connection while the other one waits to be connected to. This may be implemented by each endpoint device 102 generating a random single byte as a priority flag included in the BLE advertising data. The endpoint device 102 with the highest priority flag may initiate the connection in some embodiments. In other embodiments, the endpoint device 102 with the lowest priority flag may initiate the connection.

Each endpoint device 102 may scan its neighborhood based on two timers, $t_{scan}$ and $t_{wait}$. The timer $t_{scan}$ may set a duration of each scan while the timer $t_{wait}$ may set a duration between sequential scanning cycles. A low value for the timer $t_{wait}$ may translate to aggressive scanning which may be relatively more costly in terms of resources (e.g., network, battery). A high value for the timer $t_{wait}$ may be more efficient but may miss contact opportunities. In some embodiments, each endpoint device 102 may dynamically adapt the value of the timer $t_{wait}$ for the corresponding endpoint device 102. For example, the endpoint devices may implement the Trickle algorithm or other suitable algorithm to dynamically adapt the value of the timer $t_{wait}$. Details regarding the Trickle algorithm are disclosed in P. Levis et al., The Trickle Algorithm, RFC 6206, March 2011, DOI: 10.17487/RFC6206, which is incorporated herein by reference. In such an algorithm, a parameter $t_{trickle}$ may set a size of the window in which $t_{wait}$ would be randomly picked. At the end of a scan, if the current neighborhood is found to be consistent with the previous scan, the parameter $t_{trickle}$ may be multiplied by two, unless it hits a maximum value $t_{max}$. Whenever an inconsistency occurs, $t_{trickle}$ may be reset to a default minimum value. A neighborhood may be considered inconsistent with a previous one if a difference between two sets of peers (one for each neighborhood) is higher than a threshold Lax. Accordingly, some embodiments of the contact tracing algorithm herein may be aggressive and take advantage of any contact opportunity while an endpoint device 102 moves around and may still be "dormant" with reduced/low battery consumption when it remains idle (for instance when a user is sitting at a desk). Table 2 includes default scanning parameters according to an example embodiment:

TABLE 2

Scanning Parameters

| | |
|---|---|
| $t_{trickle}$ | 60 seconds |
| $t_{max}$ | 5 minutes |
| $t_{scan}$ | 8 seconds |
| $I_{max}$ | 2 |

After performing a scanning cycle at a given endpoint device 102, all peripherals (e.g., endpoint devices 102) found in the scan advertising the contact tracing service UUID may be added to a peer set $S_{peer}$. Peripherals that do not advertise the contact tracing service UUID may be ignored. Some example UUIDs associated with the contact tracing service in at least one embodiment are included in Table 3:

TABLE 3

Contact Tracing Service Related UUIDs

| | |
|---|---|
| service | 1e91022a-42a-434d-be23-d39eb6cd4952 |
| characteristics | 4d5c8851-6210-425f-8ab9-df679779a3b4 |

As indicated elsewhere, the endpoint devices 102 may advertise a priority flag, which may prevent dual connection. Any peer in the peer set $S_{peer}$ that lacks a priority flag or that has a priority flag that is lower than the priority flag of a given endpoint device 102 may be added to a connect set $S_{connect}$ of the given endpoint device 102. Any peer in the peer set $S_{peer}$ that has a priority flag that is higher than the priority flag of the given endpoint device 102 may be ignored by the given endpoint device 102 as the peer with the higher priority flag may initiate the connection with the given endpoint device 102.

The scan may run periodically, e.g., roughly every minute in some embodiments, and it may not be useful to connect to a peer after each scanning cycle after a connection and an exchange of ephemeral unique IDs has already been performed. In some embodiments, unless the peer's ephemeral unique ID is different such connection would bring no valuable information and may waste resources. Thus, for each peer in the connect set $S_{connect}$, the given endpoint device 102 may check if the peripheral address (e.g., the mac address) was recently successfully connected to. If a time elapsed since the last connection is less than $t_{throttle}$, the peer may be removed from the connect set $S_{connect}$ but a timestamp at which the scan occurred may be recorded in a ping table, described in more detail below.

Pings recorded in the ping table may indirectly provide amount of time spend next to a specific ephemeral unique ID. This may be useful if computing exposure time against a specific ephemeral unique ID is desired.

For each peer in the connect set $S_{connect}$, the given endpoint device 102 may connect to the peer, e.g., via BLE connection, connect to the Generic Attribute Profile (GATT) server, and proceed with the exchange of ephemeral public keys or other ephemeral unique IDs between the two devices. For example, suppose the endpoint device 102A has initiated a connection with the endpoint device 102B. After the connection is established, the endpoint device 102A may perform a GATT read query to fetch the ephemeral public key of the endpoint device 102B. After receiving the ephemeral public key of the endpoint device 102B, the endpoint device 102A may perform a GATT write query to send over the ephemeral unique ID of the endpoint device 102A to the endpoint device 102B. In some embodiments, the connection may terminate after exchanging ephemeral unique IDs. Alternatively or additionally, after the exchange of ephemeral unique IDs, each endpoint device 102A, 102B may compute a shared secret K using Elliptic Curve Diffie Hellman (ECDH) or other key agreement protocol. K may then be hashed with both keys to generate one or more private encounter tokens (PET) according to equations 5 and 6:

$$PET_1 = H_{blake2b-160}(K|PK_L) \quad \text{Equation 5}$$

$$PET_2 = H_{blake2b-160}(K|PK_R) \quad \text{Equation 6}$$

In equations 5 and 6, $PK_L$ is a local ephemeral public key, e.g., the ephemeral public key of the given endpoint device 102, and $PK_R$ is a remote ephemeral public key, e.g., the ephemeral public key of the peer endpoint device 102.

One of the PETs, referred to as the hear token, may be used to query against a database to check an infectious status of this interaction while the other one of the PETs, referred to as the tell token, may be published on the same or another database if the user of the given endpoint device 102 tests positive for infection. In some embodiments, the tell token is the PET based on the local ephemeral public key, e.g., $PET_1$ in equation 5, while the hear token is the PET based on the remote ephemeral public key, e.g., $PET_2$ in equation 6. In other embodiments, the tell token may be the PET based on the remote ephemeral public key while the hear token is the PET based on the local ephemeral public key.

One or more of the endpoint devices 102 may maintain a local database to store events and information associated with the contact tracing algorithm. The local database may be stored in storage included in or coupled to the endpoint device 102. For example, the local database of the endpoint device 102A may be stored in the storage 114. The local database of the endpoint device 102A may include one or more of a secret key 118, an ephemeral ID table 120, a tokens table 122, a ping table 124, other device IDs table 126, or an events table 128. Any of the other endpoint devices 102B-102F may include or be coupled to a similar storage with a corresponding local database specific to the endpoint device 102.

The secret key 118 may be known to both the endpoint device 102A and the backend server 110 (or more generally a network operator). The secret key 118 may be used locally by the endpoint device 102A to generate its ephemeral unique IDs, e.g., according to equations 3 and 4.

The ephemeral ID table 120 may include the ephemeral unique IDs of the endpoint device 102A, such as ephemeral public key pairs generated at the endpoint device 102A according to equations 3 and 4.

The tokens table 122 may include all unique PETs representing interactions of the endpoint device 102A with other endpoint devices 102. Alternatively or additionally, the tokens table 122 may include, for each PET, a timestamp representing a time of a corresponding interaction with another endpoint device 102. The timestamps of the PETs may be used to purge old data. For instance, the endpoint device 102A may purge PETs with timestamps greater than 3 weeks old (or other threshold) from the tokens table 122.

The ping table 124 may store each time a peripheral address is seen. Each peripheral address may be hashed.

The other device IDs table 126 may include ephemeral unique IDs of other endpoint devices 102 with which the endpoint device 102A has interacted. Alternatively or additionally, the other device IDs table 126 may include, for each ephemeral unique ID of another endpoint device 102, a timestamp representing a time at which the corresponding exchange of ephemeral unique IDs occurred between the other endpoint device 102 and the endpoint device 102A.

The events table 128 may track scan start/stop events. Alternatively or additionally, the events table 128 may track a number of endpoint devices 102 that implement the contact tracing algorithm met at each scanning cycle. Information in the events table 128 may be useful when estimating exposure risk as it may track blind spots.

When the user 106 tests positive or is aware that they have been carrying an infectious disease, the user 106 may operate their endpoint device 102 to upload their tell tokens (e.g., in the tokens table 122) from the last two weeks or other period of time to the backend server 110. The exact duration may be configurable and may depend on the specific infectious disease. The infectious tell tokens may be saved at the backend server 110 as infectious tell tokens 130.

Each endpoint device 102 may periodically upload its hear tokens to the backend server 110, which may be saved as device-specific sets of hear tokens 132 at the backend server 110. The backend server 110 may perform match-making for each endpoint device 102 (or for each user 106 associated with each endpoint device 102) by checking if any of the hear tokens in the hear token sets 132 match any of the infectious tell tokens 130. Based on the number of matches, contact duration, and/or other information, the backend server 110 may derive a risk score for the corresponding user 106 and/or endpoint device 102. Alternatively or additionally, the backend server 110 may output the risk score to the user 106 and/or may provide to the user 106 an indication of an infectious disease (or diseases) to which the user 106 was exposed, a number of exposures to the infectious disease (or diseases), a period of time covered by the risk score and/or over which the number of exposures occurred, or the like. According to this approach, each user 106 has no way of knowing which one of its interactions was infectious, which may protect the privacy of infected users 106.

In another embodiment, each endpoint device 102 may periodically download all of the infectious tell tokens 130 from the backend server 110. The endpoint device 102 may then perform match-making locally by checking if any of the infectious tell tokens 130 exists in its tokens table 122. Based on the number of matches, contact duration, and/or other information, the endpoint device 102 may derive a risk score for the corresponding user 106 and/or endpoint device 102. Alternatively or additionally, the endpoint device 102 may output the risk score to the user 106 and/or may provide to the user 106 an indication of an infectious disease (or diseases) to which the user 106 was exposed, a number of exposures to the infectious disease (or diseases), a period of time covered by the risk score and/or over which the number of exposures occurred, or the like.

In still another embodiment, each endpoint device 102 may be owned or operated by the same network operator as the backend server 110. The backend server 110 may have access to secret keys 134 of the endpoint devices 102. For example, the secret keys 134 may include the secret key 118 of the endpoint device 102A and the other endpoint devices 102 and/or may be stored in the storage 116 of the backend server 110. The backend server 110 may use the secret keys 134 to generate a set of ephemeral unique IDs for each of the endpoint devices 102, e.g., according to equations 3 and 4, which may be saved as sets of rotating IDs 136. Each set of rotating IDs 136 may be associated with a corresponding endpoint device 102 in the storage 116. Each endpoint device 102 may periodically or according to some other schedule upload a set of anonymized interactions 138 (hereinafter "interaction set 138") to the backend server 110. Each interaction set 138 may include the content of a given endpoint device's other device IDs table 126, e.g., ephemeral unique IDs (such as ephemeral public keys) of other endpoint devices 102 with which the given endpoint device 102 has interacted, a timestamp at which the corresponding exchange of ephemeral unique IDs occurred, or the like. Alternatively or additionally, each set of hear tokens 132 uploaded by a corresponding endpoint device 102 may be used as the interaction set 138 for that endpoint device 102. The backend server 110 may resolve identities of other endpoint devices 102 with which the given endpoint device 102 has interacted from the corresponding interaction set 138 of the given endpoint device 102. For example, the backend server 110 may resolve identities by, e.g., searching for each ephemeral unique ID from a corresponding interaction set 138 in the sets of rotating IDs 136. When the backend server 110 finds a given ephemeral unique ID in a given set of rotating IDs 136, the backend server 110 may determine that the endpoint device 102 with which the given endpoint device 102 interacted is the endpoint device 102 associated with the given set of rotating IDs 136.

As previously indicated, some of the endpoint devices 102 may be fixed or static and/or may be associated with known locations. For instance, the endpoint devices 102D-102F may be fixed or static. Accordingly, interactions with endpoint devices 102D-102F and similarly fixed or static endpoint devices may be used to track movement of mobile endpoint devices 102, such as the endpoint devices 102A-102C. For example, if the interaction set 138 of the endpoint device 102A includes ephemeral unique IDs of any of the fixed or static endpoint devices 102D-102F, resolving identities of the fixed or static endpoint devices 102D-102F may simultaneously resolve locations of the corresponding interactions (and thus of the mobile endpoint device 102A at the times of the interactions) if the locations of the fixed or static endpoint devices 102D-102F are known or can be determined by the backend server 110. When times of the interactions are also known (e.g., if timestamps are included for each interaction in the interaction set 138), movement patterns of the endpoint devices 102 and thus of the users 106 may be determined. The movement patterns may be used to better understand the workplace, to update the workplace to improve efficiency, or for other purposes.

Figure 2A:
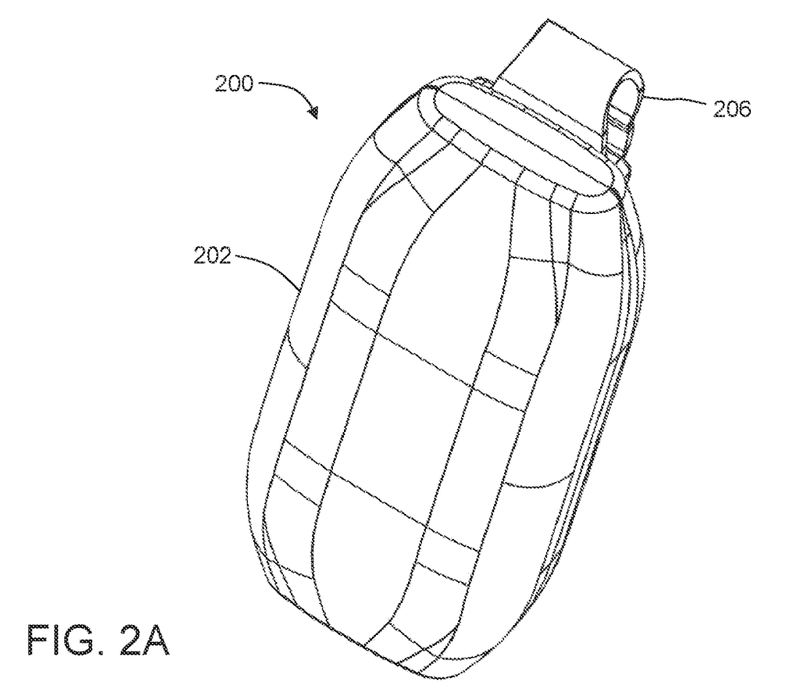
FIGS. 2A and 2B in include a top front perspective view and a bottom rear perspective view of an example endpoint device.
Figure 2B:
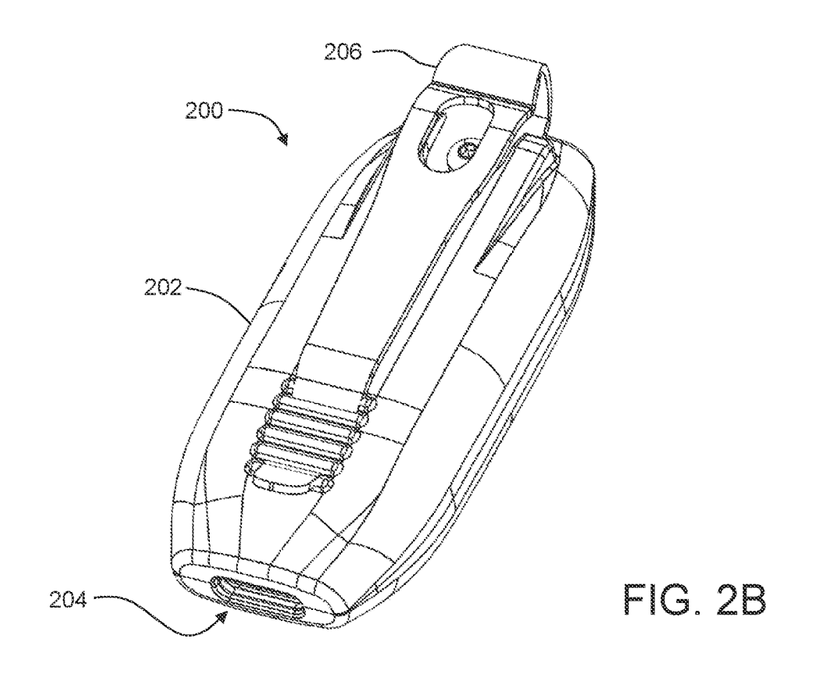

FIGS. 2A and 2B in include a top front perspective view and a bottom rear perspective view of an example endpoint device 200. The endpoint device 200 may include, be included in, or correspond to other endpoint devices described herein. Various electronics (e.g., network controller, battery, processor) may be coupled to a printed circuit board (PCB) and housed within a housing 202. The endpoint device 200 may include a charge port and/or data transfer port 204, illustrated on a bottom of the endpoint device 200 in FIG. 2B. The endpoint device 200 may include a belt clip 206 or other structure to mount or couple the endpoint device 200 to a user, the user's clothing, or the like. In other embodiments, the belt clip 206 may be omitted and the user may carry the endpoint device 200 in the user's pocket or the like.

In some embodiments, the endpoint device 200 may include one or more user input devices and/or output devices. For example, the endpoint device 200 may include one or more buttons, LEDs or other lights, haptic devices, or the like. Although not visible in FIGS. 2A and 2B, LEDs and a haptic device may be positioned within the housing 202 and coupled to the other electronics and/or the PCB. The housing 202 may be transparent at least in an area between the LEDs and an exterior of the housing 202 so that the LEDs may be perceptible to the user to receive output from the endpoint device 200. Alternatively or additionally, the haptic device may vibrate and/or vibrate according to one or more patterns, which in turn may vibrate the endpoint device 200 as a whole, which may be perceived by the user as another form of output.

For simplicity of explanation, methods described herein are depicted and described as a series of acts. However, acts in accordance with this disclosure may occur in various orders and/or concurrently, and with other acts not presented and described herein. Further, not all illustrated acts may be used to implement the methods in accordance with the disclosed subject matter. In addition, those skilled in the art will understand and appreciate that the methods may alternatively be represented as a series of interrelated states via a state diagram or events. Additionally, the methods disclosed in this specification are capable of being stored on an article of manufacture, such as a non-transitory computer-readable medium, to facilitate transporting and transferring such methods to computing devices. The term article of manufacture, as used herein, is intended to encompass a computer program accessible from any computer-readable device or storage media. Although illustrated as discrete blocks, various blocks may be divided into additional blocks, combined into fewer blocks, or eliminated, depending on the desired implementation.

Figure 3:
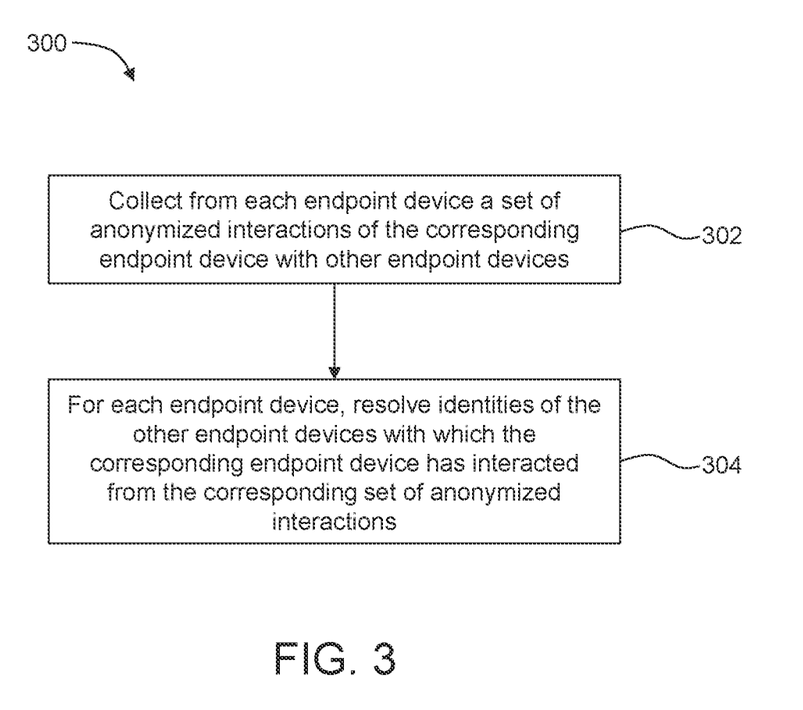
FIG. 3 illustrates a flowchart of an example method to contact trace.

FIG. 3 illustrates a flowchart of an example method 300 to contact trace, arranged in accordance with at least one embodiment described herein. The method 300 may be performed by any suitable system, apparatus, or device. For example, the backend server 110 may perform or direct performance of one or more of the operations associated with the method 300. In these and other embodiments, the method 300 may be performed or controlled by one or more processors based on one or more computer-readable instructions stored on one or more non-transitory computer-readable media. The method 300 may include one or more of blocks 302 and/or 304.

At block 302, the method 300 may include collecting, from each of multiple endpoint devices, a set of anonymized interactions of the corresponding endpoint device with other endpoint devices. For example, the backend server 110 may collect interaction sets 138 from the endpoint devices 102 of FIG. 1. Each anonymized interaction in the set of anonymized interactions may be based on an ephemeral unique ID of another endpoint device involved in a corresponding anonymized interaction with the corresponding endpoint device. For example, the interaction set 138 of the endpoint device 102A may include multiple interactions between the endpoint device 102A and other endpoint devices 102, where each interaction includes ephemeral unique IDs of the other endpoint devices 102 that may have been stored in the other device IDs table 126. Block 302 may be followed by block 304.

At block 304, the method 300 may include, for each endpoint device, resolving identities of the other endpoint devices with which the corresponding endpoint device has interacted from the corresponding set of anonymized interactions. In some embodiments, the method 300 further includes precomputing ephemeral unique IDs for each endpoint device and storing the precomputed ephemeral unique IDs for each endpoint device, e.g., as a corresponding set of rotating IDs 136 in the storage 116. In this and other embodiments, each anonymized interaction may include an ephemeral unique ID of a corresponding one of the other endpoint devices with which the corresponding device has interacted. Alternatively or additionally, resolving identities of the other endpoint devices with which the corresponding device has interacted at block 304 may include searching for ephemeral unique IDs from the anonymized interactions in the stored precomputed ephemeral unique IDs.

In some embodiments, resolving identities of the other endpoint devices with which the corresponding device has interacted at block 304 may further include, in response to a given anonymized interaction matching a given stored precomputed ephemeral unique ID that is associated with a given endpoint device, determining that the corresponding endpoint device interacted with the given endpoint device. For example, if an ephemeral unique ID from the other device IDs table 126 of the endpoint device 102A matches a precomputed ephemeral unique ID in the set of rotating IDs 136 for the endpoint device 102B, the backend server 110 may determine that the endpoint device 102A interacted with the endpoint device 102B.

In some embodiments, each endpoint device has a corresponding secret key known to a network operator and each ephemeral unique ID is precomputed based at least in part on a corresponding secret key and a counter. For example, each of the endpoint devices 102 may include a secret key (such as the secret key 118 of the endpoint device 102A), all of which may be stored as secret keys 134 at the backend server 110. The backend server 110 may also have or know the time parameters of equation 2 to determine values for the counter C or may simply use a series of integers for the counter C. Using the secret keys 134 of the endpoint devices 102 and the counter C, the backend server 110 may precompute, for each of the endpoint devices 102, a corresponding set of rotating IDs 136.

Precomputing ephemeral unique IDs may include, for each endpoint device, generating multiple deterministic seeds from the corresponding secret key and multiple counter values, and generating multiple ephemeral public key pairs from the deterministic seeds. Each precomputed ephemeral unique ID may include a different one of the ephemeral public key pairs. For example, the backend server 110 may generate the deterministic seeds according to equation 3, e.g., by generating hash values where each hash value is a hash of the corresponding secret key and a different counter value. Alternatively or additionally, the backend server 110 may generate the ephemeral public key pairs according to equation 4, e.g., by generating Curve25519 public keys where each Curve25519 public key is generated using a different deterministic seed as input.

In some embodiments, the method 300 may further include determining whether a first user of the corresponding endpoint device was exposed to a second user of another endpoint device based on whether an identity of the other endpoint device is among the resolved identities of the other endpoint devices with which the corresponding endpoint device has interacted.

In some embodiments, the endpoint devices may be borne by users at a job site. The method 300 may further include determining, based on interactions with endpoint devices having known locations within the job site, at least one of: one or more patterns of movement of the users at the job site; analytics regarding frequency of visits by users to each of one or more locations within the job site; or analytics regarding number of interactions between the users at each of one or more locations within the job site.

Figure 4:
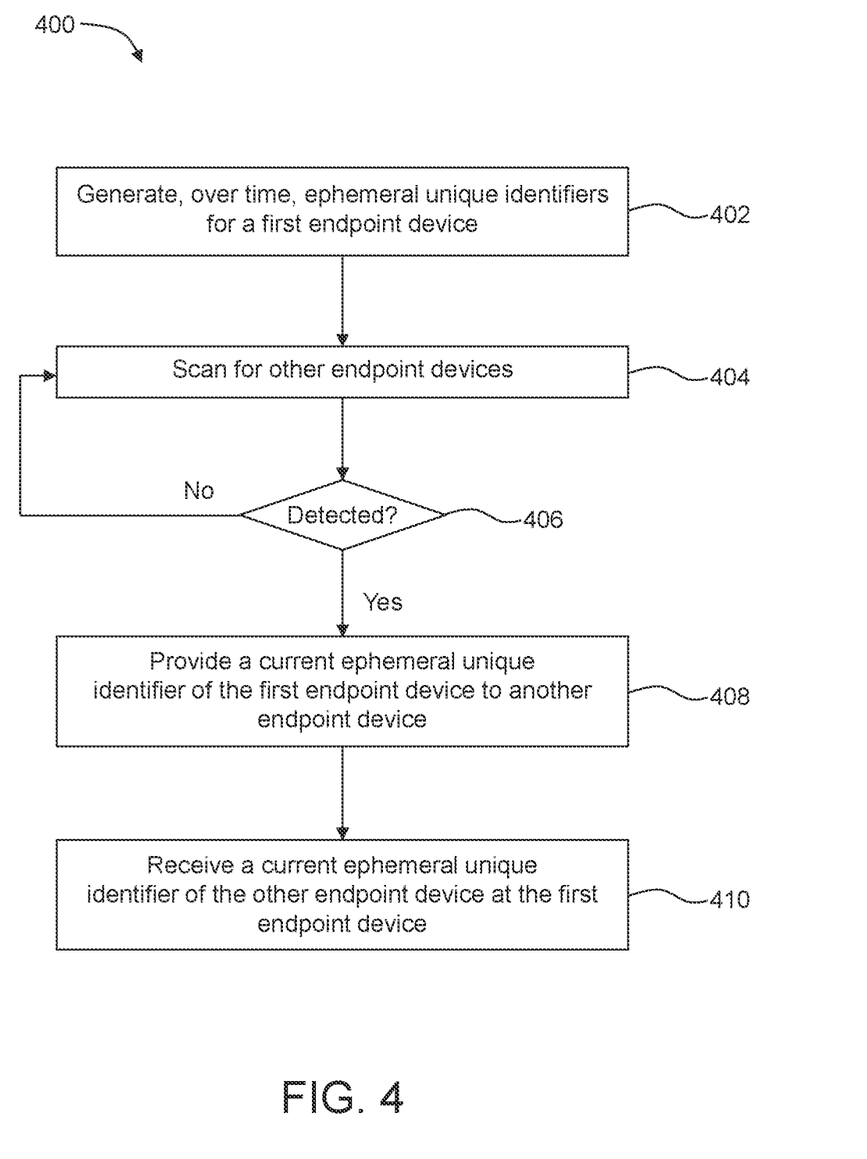
FIG. 4 illustrates a flowchart of another example method to contact trace.

FIG. 4 illustrates a flowchart of another example method 400 to contact trace, arranged in accordance with at least one embodiment described herein. The method 400 may be performed by any suitable system, apparatus, or device. For example, one or more of the endpoint devices 102, 200 may perform or direct performance of one or more of the operations associated with the method 400. In these and other embodiments, the method 400 may be performed or controlled by one or more processors based on one or more computer-readable instructions stored on one or more non-transitory computer-readable media. The method 400 may include one or more of blocks 402, 404, 406, 408, and/or 410.

At block 402, the method 400 may include generating, over time, multiple ephemeral unique IDs for a first endpoint device. Each of the ephemeral unique IDs may be specific to the endpoint device and may be configured to identify the first endpoint device. For example, the endpoint device 102A may periodically or according to some other schedule generate an ephemeral unique ID at a given time now and add it to the ephemeral ID table 120.

At block 404, the method 400 may include scanning for other endpoint devices. For example, the endpoint device 102A may periodically or according to some other schedule scan its neighborhood for other endpoint devices 102. In some embodiments, the scan may have a duration of $t_{scan}$ with a duration of $t_{wait}$ between scans. Alternatively or additionally, the duration $t_{wait}$ may be dynamically adapted, e.g., based on the Trickle algorithm.

At block 406, the method 400 may include determining whether another endpoint device has been detected while scanning. If another endpoint device is not detected at block 406, the method 400 may return to block 404. If another endpoint device is detected at block 406, the method may proceed to block 408. For example, if the endpoint device 102A detects the endpoint device 102B in its scan, the method 400 may proceed to block 408.

At block 408, and in response to detecting another endpoint device, e.g., a second endpoint device, while scanning, the method 400 may include providing a current ephemeral unique ID of the first endpoint device to the second endpoint device. For example, if the endpoint device 102A detects the endpoint device 102B during a scan of its neighborhood, the endpoint device 102A may provide its current ephemeral unique ID to the endpoint device 102B. In some embodiments, the endpoint device 102A performs a GATT write query to send its current ephemeral unique ID to the endpoint device 102B. In some embodiments, the endpoint device 102A provides its current ephemeral unique ID to the endpoint device 102B in response to a GATT read query from the endpoint device 102B.

At block 410, the method 400 may further include receiving a current ephemeral unique ID of the second endpoint device at the first endpoint device. For example, the endpoint device 102A may receive a current ephemeral unique ID of the second endpoint device. In some embodiments, the endpoint device 102A performs a GATT read query to fetch the current ephemeral public key of the endpoint device 102B. In some embodiments, the endpoint device 102A receives the current ephemeral unique ID of the endpoint device 102B as a result of the endpoint device 102B performing a GATT write query.

In some embodiments, the method 400 may further include adding an anonymized interaction with the second endpoint device to a set of anonymized interactions of the first endpoint device with other endpoint devices. Each anonymized interaction in the set of anonymized interactions may be based on a corresponding ephemeral unique ID of the corresponding endpoint device received during a corresponding interaction between the first endpoint device and the corresponding endpoint device. In some embodiments, each anonymized interaction includes one or more tokens and/or may be stored in, e.g., the tokens table 122 of the corresponding endpoint device 102. In some embodiments, each anonymized interaction includes an ephemeral unique ID of the corresponding endpoint device with which the first endpoint device interacted and/or may be stored in, e.g., the other device IDs table 126.

In some embodiments, the method 400 may further include sharing the set of anonymized interactions of the first endpoint device with a backend server to resolve identities of the other endpoint devices with which the first endpoint device has interacted. For example, the endpoint device 102A may share the contents of its other device IDs table 126 with the backend server 110 for the backend server 110 to resolve identities of other endpoint devices 102 with which the endpoint device 102A has interacted.

In some embodiments, the first endpoint device has a secret key known to a network operator and each of the ephemeral unique identifiers for the first endpoint device is based on the secret key and a counter. In these and other embodiments, generating, over time, the ephemeral unique identifiers may include, for each of the ephemeral unique identifiers, generating a deterministic seed and generating an ephemeral public key pair. The deterministic seed may be generated from the secret key and a counter value that depends on a time at which the deterministic seed is generated, e.g., according to equation 3. The ephemeral public key pair may be generated from the deterministic seed to use as a corresponding one of the ephemeral unique identifiers, e.g., according to equation 4. In some embodiments, generating the deterministic seed may include generating a hash value as a hash of the secret key and the counter value. In some embodiments, the counter value includes a value of a difference between a current time and a reference time divided by a time step, e.g., according to equation 2. Alternatively or additionally, generating the ephemeral public key pair may include generating a Curve25519 public key using the deterministic seed as input.

In some embodiments, the method 400 may further include determining a distance between the first endpoint device and the second endpoint device. In response to the distance being less than a threshold, the method 400 may further include outputting an alert to a user of the first endpoint device. For example, the endpoint device 400 may vibrate, turn on one or more LEDs, or provide other output to the user as an alert. The threshold may depend on one or more infections of concern. For example, during the covid-19 pandemic that began around the beginning of 2020, individuals were advised to social distance, e.g., to remain more than 6 feet (about 2 meters) from other individuals not of their household to reduce the risk of infection. Accordingly, the threshold may be set to 6 feet or other threshold. In this and other examples, the alert may serve to remind the user to distance themselves further from other users in proximity to the user.

Figure 5:
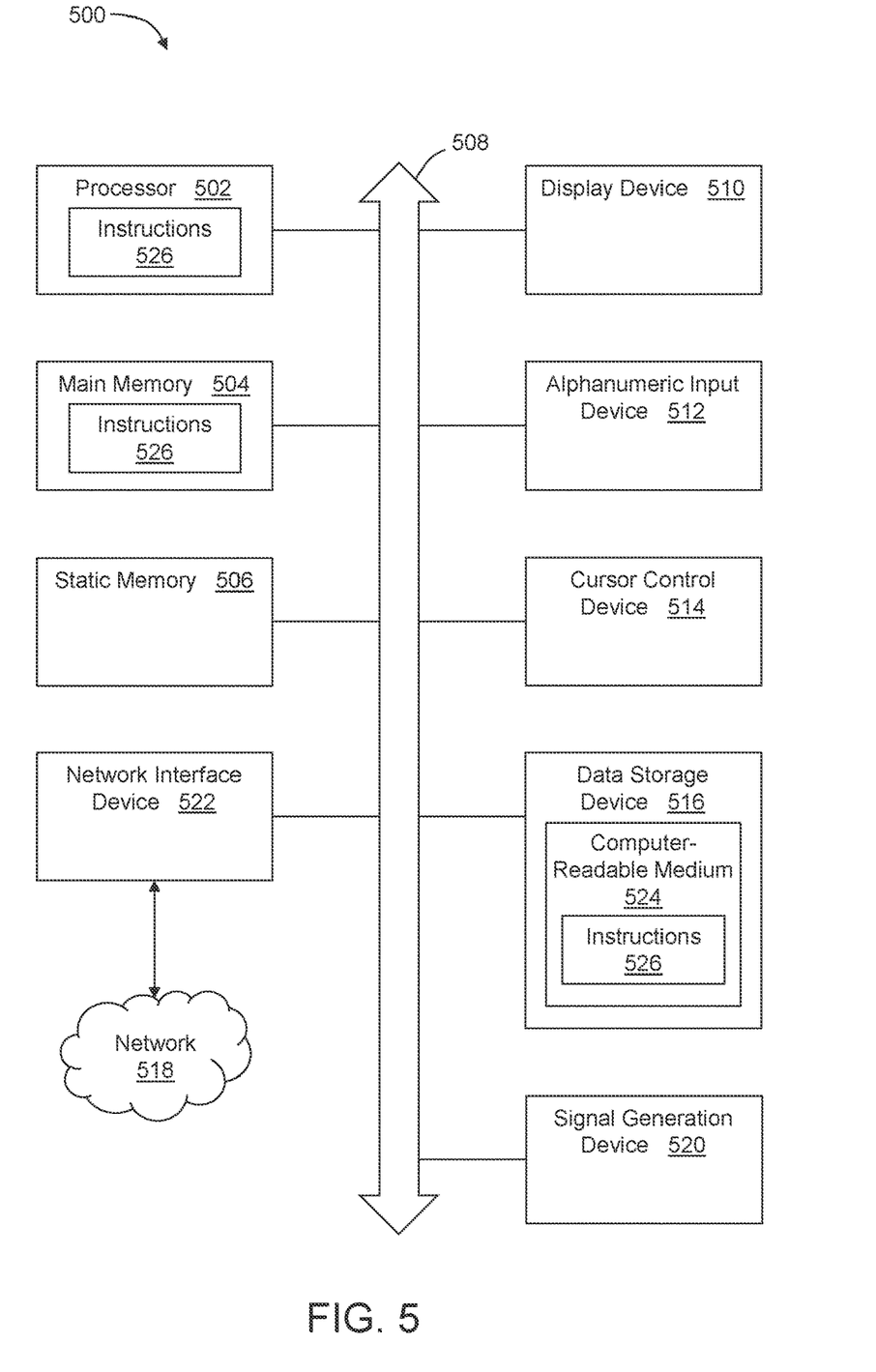
FIG. 5 illustrates a diagrammatic representation of a machine in the example form of a computing device within which a set of instructions, for causing the machine to perform any one or more of the methods discussed herein, may be executed.

FIG. 5 illustrates a diagrammatic representation of a machine in the example form of a computing device 500 within which a set of instructions, for causing the machine to perform any one or more of the methods discussed herein, may be executed. For example, the computing device 500 may include, be included in, or correspond to any of the endpoint devices 102, 200 or backend server 110 described herein. The computing device 500 may include a mobile phone, a smart phone, a netbook computer, a rackmount server, a router computer, a server computer, a personal computer, a mainframe computer, a laptop computer, a tablet computer, a desktop computer etc., within which a set of instructions, for causing the machine to perform any one or more of the methods discussed herein, may be executed. In alternative embodiments, the machine may be connected (e.g., networked) to other machines in a LAN, an intranet, an extranet, or the Internet. The machine may operate in the capacity of a server machine in client-server network environment. The machine may include a personal computer (PC), a set-top box (STB), a server, a network router, switch or bridge, or any machine capable of executing a set of instructions (sequential or otherwise) that specify actions to be taken by that machine. Further, while only a single machine is illustrated, the term "machine" may also include any collection of machines that individually or jointly execute a set (or multiple sets) of instructions to perform any one or more of the methods discussed herein.

The example computing device 500 includes a processing device (e.g., a processor) 502, a main memory 504 (e.g., read-only memory (ROM), flash memory, dynamic random access memory (DRAM) such as synchronous DRAM (SDRAM)), a static memory 506 (e.g., flash memory, static random access memory (SRAM)) and a data storage device 516, which communicate with each other via a bus 508.

Processing device 502 represents one or more general-purpose processing devices such as a microprocessor, central processing unit, or the like. More particularly, the processing device 502 may include a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 502 may also include one or more special-purpose processing devices such as an application specific integrated circuit (ASIC), a field programmable gate array (FPGA), a digital signal processor (DSP), network processor, or the like. The processing device 502 is configured to execute instructions 526 for performing the operations and steps discussed herein.

The computing device 500 may further include a network interface device 522 which may communicate with a network 518. The network 518 may include, be included in, or correspond to the network 112 of FIG. 1. The computing device 500 also may include a display device 510 (e.g., a liquid crystal display (LCD) or a cathode ray tube (CRT)), an alphanumeric input device 512 (e.g., a keyboard), a cursor control device 514 (e.g., a mouse) and a signal generation device 520 (e.g., a speaker). In at least one embodiment, the display device 510, the alphanumeric input device 512, and the cursor control device 514 may be combined into a single component or device (e.g., an LCD touch screen).

The data storage device 516 may include a computer-readable storage medium 524 on which is stored one or more sets of instructions 526 embodying any one or more of the methods or functions described herein. The instructions 526 may also reside, completely or at least partially, within the main memory 504 and/or within the processing device 502 during execution thereof by the computing device 500, the main memory 504 and the processing device 502 also constituting computer-readable media. The instructions 526 may further be transmitted or received over the network 518 via the network interface device 522.

While the computer-readable storage medium 526 is shown in an example embodiment to be a single medium, the term "computer-readable storage medium" may include a single medium or multiple media (e.g., a centralized or distributed database and/or associated caches and servers) that store the one or more sets of instructions. The term "computer-readable storage medium" may also include any medium that is capable of storing, encoding or carrying a set of instructions for execution by the machine and that cause the machine to perform any one or more of the methods of the present disclosure. The term "computer-readable storage medium" may accordingly be taken to include, but not be limited to, solid-state memories, optical media and magnetic media.

Terms used herein and especially in the appended claims (e.g., bodies of the appended claims) are generally intended as "open" terms (e.g., the term "including" may be interpreted as "including, but not limited to," the term "having" may be interpreted as "having at least," the term "includes" may be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases may not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" may be interpreted to mean "at least one" or "one or more"); the same holds true for the use of definite articles used to introduce claim recitations.

In addition, even if a specific number of an introduced claim recitation is explicitly recited, those skilled in the art will recognize that such recitation may be interpreted to mean at least the recited number (e.g., the bare recitation of "two recitations," without other modifiers, means at least two recitations, or two or more recitations). Further, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, may be understood to contemplate the possibilities of including one of the terms, either of the terms, or both terms. For example, the phrase "A or B" may be understood to include the possibilities of "A" or "B" or "A and B."

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM)

or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions may include, for example, instructions and data which cause a general purpose computer, special purpose computer, or special purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general purpose hardware (e.g., computer-readable media, processing devices, etc.) of the computing system. In some embodiments, the different components, modules, engines, and services described herein may be implemented as objects or processes that execute on the computing system (e.g., as separate threads). While some of the system and methods described herein are generally described as being implemented in software (stored on and/or executed by general purpose hardware), specific hardware implementations or a combination of software and specific hardware implementations are also possible and contemplated. In this description, a "computing entity" may be any computing system as previously defined herein, or any module or combination of modulates running on a computing system.

For the processes and/or methods disclosed, the functions performed in the processes and methods may be implemented in differing order as may be indicated by context. Furthermore, the outlined steps and operations are only provided as examples, and some of the steps and operations may be optional, combined into fewer steps and operations, or expanded into additional steps and operations.

This disclosure may sometimes illustrate different components contained within, or connected with, different other components. Such depicted architectures are merely examples, and many other architectures can be implemented which achieve the same or similar functionality.

Aspects of the present disclosure may be embodied in other forms without departing from its spirit or essential characteristics. The described aspects are to be considered in all respects illustrative and not restrictive. The claimed subject matter is indicated by the appended claims rather than by the foregoing description. All changes which come within the meaning and range of equivalency of the claims are to be embraced within their scope.

What is claimed is:

1. A method, comprising:
   collecting from each endpoint device of a plurality of endpoint devices a set of anonymized interactions of a corresponding endpoint device with other endpoint devices, wherein each anonymized interaction in the set of anonymized interactions is based on an ephemeral unique identifier of another endpoint device involved in a corresponding anonymized interaction with the corresponding endpoint device;
   for each endpoint device, resolving identities of the other endpoint devices with which the corresponding endpoint device has interacted from the corresponding set of anonymized interactions;
   precomputing ephemeral unique identifiers for each endpoint device; and
   storing the precomputed ephemeral unique identifiers for each endpoint device, wherein:
   each anonymized interaction includes an ephemeral unique identifier of a corresponding one of the other endpoint devices with which the corresponding device has interacted; and
   resolving identities of the other endpoint devices with which the corresponding device has interacted comprises searching for ephemeral unique identifiers from the anonymized interactions in the stored precomputed ephemeral unique identifiers.

2. The method of claim 1, wherein resolving identities of the other endpoint devices with which the corresponding device has interacted further comprises, in response to a given anonymized interaction matching a given stored precomputed ephemeral unique identifier that is associated with a given endpoint device, determining that the corresponding endpoint device interacted with the given endpoint device.

3. The method of claim 1, wherein:
   each endpoint device has a corresponding secret key known to a network operator; and
   each ephemeral unique identifier is precomputed based at least in part on a corresponding secret key and a counter.

4. The method of claim 3, wherein precomputing ephemeral unique identifiers comprises, for each endpoint device:
   generating a plurality of deterministic seeds from the corresponding secret key and a plurality of counter values; and
   generating a plurality of ephemeral public key pairs from the plurality of deterministic seeds, wherein each precomputed ephemeral unique identifier comprises a different one of the plurality of ephemeral public key pairs.

5. The method of claim 4, wherein generating the plurality of deterministic seeds comprises generating a plurality of hash values, each hash value being a hash of the corresponding secret key and a different counter value of the plurality of counter values.

6. The method of claim 4, wherein generating the plurality of ephemeral public key pairs
   comprises generating a plurality of Curve25519 public keys, each Curve25519 public key generated using a different deterministic seed of the plurality of deterministic seeds as input.

7. The method of claim 1, further comprising determining whether a first user of the corresponding endpoint device was exposed to a second user of another endpoint device based on whether an identity of the other endpoint device is among the resolved identities of the other endpoint devices with which the corresponding endpoint device has interacted.

8. The method of claim 1, wherein the plurality of endpoint devices are borne by users at a job site, the method further comprising determining, based on a plurality of interactions with endpoint devices having known locations within the job site, at least one of:
   one or more patterns of movement of the users at the job site;

analytics regarding frequency of visits by users to each of one or more locations within the job site; or analytics regarding number of interactions between the users at each of one or more locations within the job site.

9. A non-transitory computer-readable storage medium having computer-readable instructions stored thereon that are executable by a processor to cause a system to perform operations comprising:

collect from each endpoint device of a plurality of endpoint devices a set of anonymized interactions of a corresponding endpoint device with other endpoint devices, wherein each anonymized interaction in the set of anonymized interactions is based on an ephemeral unique identifier of another endpoint device involved in a corresponding anonymized interaction with the corresponding endpoint device;

for each endpoint device, resolve identities of the other endpoint devices with which the corresponding endpoint device has interacted from the corresponding set of anonymized interactions;

precompute ephemeral unique identifiers for each endpoint device; and store the precomputed ephemeral unique identifiers for each endpoint device, wherein:

each anonymized interaction includes an ephemeral unique identifier of a corresponding one of the other endpoint devices with which the corresponding device has interacted; and wherein when resolving identities of the other endpoint devices with which the corresponding device has interacted the system is configured to search for ephemeral unique identifiers from the anonymized interactions in the stored precomputed ephemeral unique identifiers.

10. A method, comprising:

generating, over time, a plurality of ephemeral unique identifiers for a first endpoint device, wherein each of the plurality of ephemeral unique identifiers is specific to the first endpoint device and is configured to identify the first endpoint device;

scanning for other endpoint devices;

in response to detecting a second endpoint device while scanning:

providing a current ephemeral unique identifier of the first endpoint device to the second endpoint device; and receiving a current ephemeral unique identifier of the second endpoint device at the first endpoint device; and adding an anonymized interaction with the second endpoint device to a set of anonymized interactions of the first endpoint device with other endpoint devices, each anonymized interaction in the set of anonymized interactions based on a corresponding ephemeral unique identifier of a corresponding endpoint device received during a corresponding interaction between the first endpoint device and the corresponding endpoint device.

11. The method of claim 10, further comprising sharing the set of anonymized interactions of the first endpoint device with a backend server to resolve identities of the other endpoint devices with which the first endpoint device has interacted.

12. The method of claim 10, wherein:

the first endpoint device has a secret key known to a network operator; and each of the plurality of ephemeral unique identifiers for the first endpoint device is based on the secret key and a counter.

13. The method of claim 12, wherein generating, over time, the plurality of ephemeral unique identifiers comprises, for each of the plurality of ephemeral unique identifiers:

generating a deterministic seed from the secret key and a counter value that depends on a time at which the deterministic seed is generated; and generating an ephemeral public key pair from the deterministic seed to use as a corresponding one of the plurality of ephemeral unique identifiers.

14. The method of claim 13, wherein generating the deterministic seed comprises generating a hash value as a hash of the secret key and the counter value.

15. The method of claim 13, wherein the counter value comprises a value of a difference between a current time and a reference time divided by a time step.

16. The method of claim 13, wherein generating the ephemeral public key pair comprises generating a Curve25519 public key using the deterministic seed as input.

17. The method of claim 10, further comprising:

determining a distance between the first endpoint device and the second endpoint device; and in response to the distance being less than a threshold, outputting an alert to a user of the first endpoint device.

18. A non-transitory computer-readable storage medium having computer-readable instructions stored thereon that are executable by a processor to cause a system to perform operations comprising:

generate, over time, a plurality of ephemeral unique identifiers for a first endpoint device, wherein each of the plurality of ephemeral unique identifiers is specific to the first endpoint device and is configured to identify the first endpoint device;

scan for other endpoint devices; and in response to detecting a second endpoint device while scanning:

provide a current ephemeral unique identifier of the first endpoint device to the second endpoint device; and receive a current ephemeral unique identifier of the second endpoint device at the first endpoint device; and add an anonymized interaction with the second endpoint device to a set of anonymized interactions of the first endpoint device with other endpoint devices, each anonymized interaction in the set of anonymized interactions based on a corresponding ephemeral unique identifier of a corresponding endpoint device received during a corresponding interaction between the first endpoint device and the corresponding endpoint device.

* * * * *